(12) United States Patent
McLeod et al.

(10) Patent No.: US 6,561,991 B2
(45) Date of Patent: May 13, 2003

(54) NON-INVASIVE METHOD AND SYSTEM OF QUANTIFYING HUMAN POSTURAL STABILITY

(75) Inventors: Kenneth J. McLeod, Stony Brook, NY (US); Clinton T. Rubin, Port Jefferson, NY (US)

(73) Assignee: The Research Foundation of the State University of New York (SUNY), Stony Brook, NY (US)

( * ) Notice: Subject to any disclaimer, the term of this patent is extended or adjusted under 35 U.S.C. 154(b) by 11 days.

(21) Appl. No.: 09/739,222

(22) Filed: Dec. 19, 2000

(65) Prior Publication Data

US 2002/0077567 A1 Jun. 20, 2002

(51) Int. Cl.⁷ .......................... A61B 5/103; A61B 5/117
(52) U.S. Cl. ........................................ 600/587; 600/552
(58) Field of Search ............................... 600/587, 592, 600/594, 595, 552, 590

(56) References Cited

U.S. PATENT DOCUMENTS

| | | | |
|---|---|---|---|
| 4,195,643 A | * 4/1980 | Pratt, Jr. ............... | 128/779 |
| 5,103,806 A | 4/1992 | McLeod et al. ........ | 128/24 AA |
| 5,125,412 A | * 6/1992 | Thornton ............... | 128/670 |
| 5,191,880 A | 3/1993 | McLeod et al. ........ | 128/24 AA |
| 5,271,416 A | * 12/1993 | Lepley .................. | 128/782 |
| 5,273,028 A | 12/1993 | McLeod et al. ........ | 128/33 |
| 5,337,757 A | * 8/1994 | Jain et al. .............. | 128/779 |
| 5,376,065 A | 12/1994 | McLeod et al. ........ | 601/98 |
| 5,412,987 A | 5/1995 | Bergstrom et al. .... | 73/517 R |
| 5,662,118 A | * 9/1997 | Skubick ................ | 128/733 |
| 5,964,719 A | * 10/1999 | Costello et al. ....... | 600/595 |
| 6,234,975 B1 | * 5/2001 | McLeod et al. ....... | 600/552 |

FOREIGN PATENT DOCUMENTS

WO      WO 99/07280      2/1999

* cited by examiner

Primary Examiner—Charles G. Freay
Assistant Examiner—Han L. Liu
(74) Attorney, Agent, or Firm—Dilworth & Barrese, LLP

(57) ABSTRACT

A non-invasive method for evaluating a musculoskeletal system of a patient is provided which includes the steps of: providing a vibration measurement device in proximity to a non-rigidly supported platform; measuring a vibrational response of the patient's musculoskeletal system using the vibration measurement device after the patient rests on the non-rigidly supported platform; performing a frequency decomposition of the vibrational response to quantify the vibrational response into specific vibrational spectra; and analyzing the vibrational spectra to evaluate muscle strength, postural stability and bone density. A non-invasive physiologic vibration quantification system is also provided for evaluating the musculoskeletal system of the patient. The system includes vibration means for externally transferring vibrations to the musculoskeletal system and including a vibration measurement device for measuring a response by the musculoskeletal system in accordance with the vibrations transferred by the vibration means and for forming signals representative of the musculoskeletal system response; and an analyzer coupled to the vibration measurement device for receiving the signals from the vibration measurement device and developing a frequency spectrum associated with the signals. The frequency spectrum provides vibrational quantification of the musculoskeletal system for evaluating at least postural stability.

16 Claims, 6 Drawing Sheets

NON-INVASIVE METHOD AND SYSTEM OF QUANTIFYING HUMAN POSTURAL STABILITY

BACKGROUND OF THE INVENTION

1. Technical Field

This disclosure relates to a method and system for physiologic vibration quantification and, more particularly, to a method and system for quantifying postural sway to determine postural instability or imbalance.

2. Description of the Related Art

Falls represent a serious medical problem in the United States. As one example, consider that some 250,000 individuals fall each year fracturing their hip. This generally results in total hip arthroplasty or hip replacement surgery at a significant cost. Health care costs in this area range in the billions of dollars per year in the United States alone. Further, the morbidity associated with hip fractures is extensive. Half of all individual who undergo total hip arthroplasty will not achieve their previous level of motility and will require assistance to walk. Moreover, for patients over 70, more than one-half will die within 12 months of a hip fracture due to complications associated with the surgery or extended bed rest following surgery. Other consequences as a result of falling include lost wages, lost productivity, upper extremity injuries, head injuries, fear of falling leading to decreased physical activity, etc.

The primary cause of falling is loss of balance, and the inability to re-achieve balance once it is lost, concepts referred to as postural instability or imbalance. Postural instability is closely tied to the status of the neuro-muscular system, though a thorough understanding of the factors that lead to, or detract from, postural stability has yet to be established.

While all of the physiologic factors ensuring postural stability are not necessarily known, it is still possible to quantify postural stability. A number of methodology and measures have been proposed to characterize postural sway. The majority of the approaches rely on. "force plates" or pressure sensitive detectors to identify the redistribution of body weight at the feet, though alternative approaches, (e.g. upper body position detection) have been proposed. These devices are sometimes utilized with the patient standing quietly on a rigid surface, but also, active perturbation of the patient can be imposed and recovery from the perturbation evaluated.

Analysis of the postural sway data can be done in the time domain, for example, evaluation of peak—peak sway magnitude. Analysis can also be done in the frequency domain which includes sophisticated stabilogram-diffusion analysis, as well as spectral analysis procedures. Frequency domain analysis approaches have led to the observation that the decrease in postural stability in the elderly is associated with a change in the slope of the spectral content of the postural sway.

However, such frequency spectra can be difficult to interpret as individuals can rely on a variety of strategies to maintain postural stability. For example, young adults are quite capable of standing quietly with little postural sway, though some young adults permit themselves to undergo extensive body sway excursion without fear of falling due to their superior postural stability. Spectral sway analysis procedures which do not account for such phenomena can lead to an incorrect diagnosis of sway condition.

Accordingly, a method and system are needed for quantifying postural sway to determine postural instability or imbalance of individuals.

SUMMARY OF THE INVENTION

The present disclosure describes a method and system for accurately and reproducibly characterizing postural sway to determine postural instability or imbalance. The method entails recording postural stability while the individual is standing on a non-rigidly supported platform of a postural quantifying system of the present disclosure.

The method of the present disclosure provides two distinct features. First, the intrinsic instability of the non-rigid platform forces the individuals to control their posture in dynamic, rather than static situation, so that a more accurate determination of postural stability is obtained. Second, By utilizing a moving platform, position, velocity or acceleration sensors can be used in place of force sensors as used in prior art systems, thus allowing less expensive system construction.

In particular, the present disclosure provides a non-invasive method for evaluating a musculoskeletal system of a patient including the steps of: providing a vibration measurement device in proximity to a non-rigidly supported platform; measuring a vibrational response of the patient's musculoskeletal system using the vibration measurement device after the patient rests on the non-rigidly supported platform; performing a frequency decomposition of the vibrational response to quantify the vibrational response into specific vibrational spectra; and analyzing the vibrational spectra to evaluate at least postural stability.

The present disclosure also provides a non-invasive physiologic vibration quantification system for evaluating a musculoskeletal system of a patient undergoing controlled mechanical perturbation. The system includes vibration means for externally transferring vibrations to the musculoskeletal system and including a vibration measurement device for measuring a response by the musculoskeletal system in accordance with the vibrations transferred by the vibration means and for forming signals representative of the musculoskeletal system response; and an analyzer coupled to the vibration measurement device for receiving the signals from the vibration measurement device and developing a frequency spectrum associated with the signals. The frequency spectrum provides vibrational quantification of the musculoskeletal system for evaluating at least postural stability.

BRIEF DESCRIPTION OF THE DRAWINGS

The invention will be described in detail in the following description of preferred embodiments with reference to the following figures wherein.

DETAILED DESCRIPTION OF PREFERRED EMBODIMENTS

Figure 1:
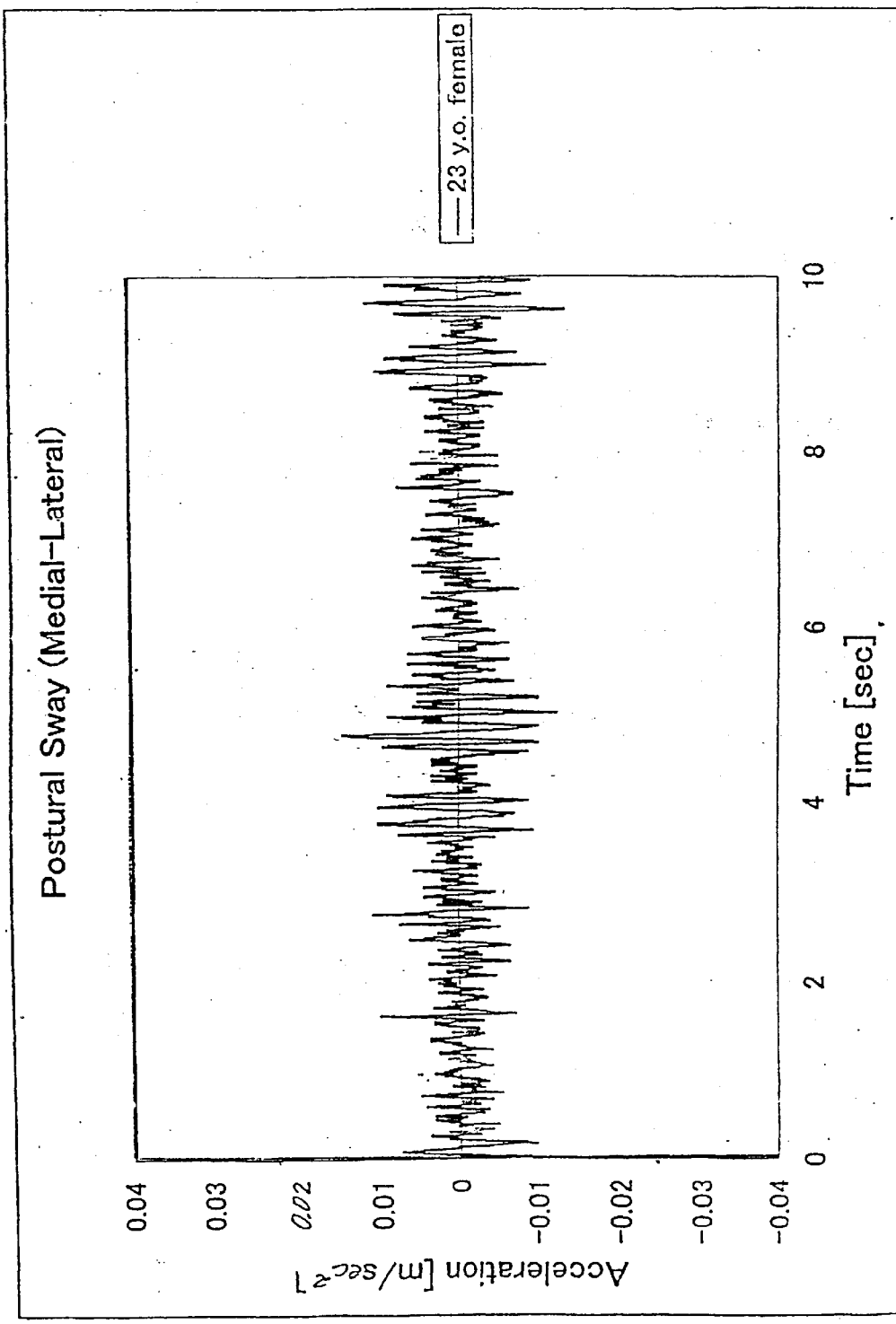
FIGS. 1 and 2 are charts illustrating the time-dependent sway characteristics of a 23 year old woman to a 54 year old woman obtained by the method and system of the present disclosure.

The present disclosure describes a method and system for accurately and reproducibly characterizing postural sway to determine postural instability or imbalance. In a preferred embodiment, an individual stands on a non-rigidly supported platform with an accelerometer attached on the outboard side of the platform so that the accelerometer is capable of sensing medial-lateral sway.

The standing platform rests on motorized spring mechanisms which cause the platform to move when they are turned on. Alternatively, the standing platform may rest on a plurality of springs or coils which cause the standing platform to move once a patient stands thereon. Further, the standing platform can include various compliant modalities other than springs (e.g., rubber, elastomerics, foams, etc). The movement of the standing platform enables the accelerometer to sense the medial-lateral sway of the patient's body.

In one embodiment, a cantilever beam accelerometer is used which typically employs a cantilever with one end supported on a mount and a proof mass on the other. Such a beam is typically micro-machined from silicon, and one or more strain gauges disposed on its surface at a desired sensing site. These one or more strain gauges are connected in an electric circuit to provide a signal indicative of acceleration-induced strain in the beam. The proof mass used is low in order to allow measurements at higher frequencies, since the natural frequency of the beam varies as the inverse square root of the mass. Cantilever beam strain gauge accelerometers are desirable because of their high sensitivity and their frequency response which extends down to D.C. See, e.g. U.S. Pat. No. 5,412,987 to Bergstrom et al. which is incorporated herein by reference. Alternatively, low cost solid state, variable capacitance accelerometers may be used, which, while less sensitive, are more robust.

The accelerometer records the individual's natural sway pattern while the individual preferably stands in the Romberg position (feet separated at shoulder width, hands at side, and eyes open) for a preferable period of 10–100 seconds. The acceleration data is amplified, filtered using signal processing techniques to remove signal contributions above 15 Hz, and then digitized at sampling rates preferably exceeding 50 Hz. Spectral analysis of the data is obtained using fast fourier transform techniques, and the acceleration spectra are converted to displacement spectra over the preferable frequency range of 0.01 Hz to 10 Hz.

In several embodiments, the resonance of the spring-mass system of the sprung non-rigid platform and the patient produces a resonance between 5–10 Hz which can confound the analysis. Therefore, the frequencies above approximately 3 Hz are not used in the analysis. Frequencies in the range of 0.5–3 Hz are typically used to determine postural sway.

The analysis extracts out a single measurement which is characteristic of the postural stability of the individual. Accordingly, the analysis is capable of demonstrating the age dependent changes in postural sway, and can identify individuals with orthopaedic problems. In addition, the analysis demonstrates the ability of low-level mechanical vibration to influence postural stability.

Figure 2:
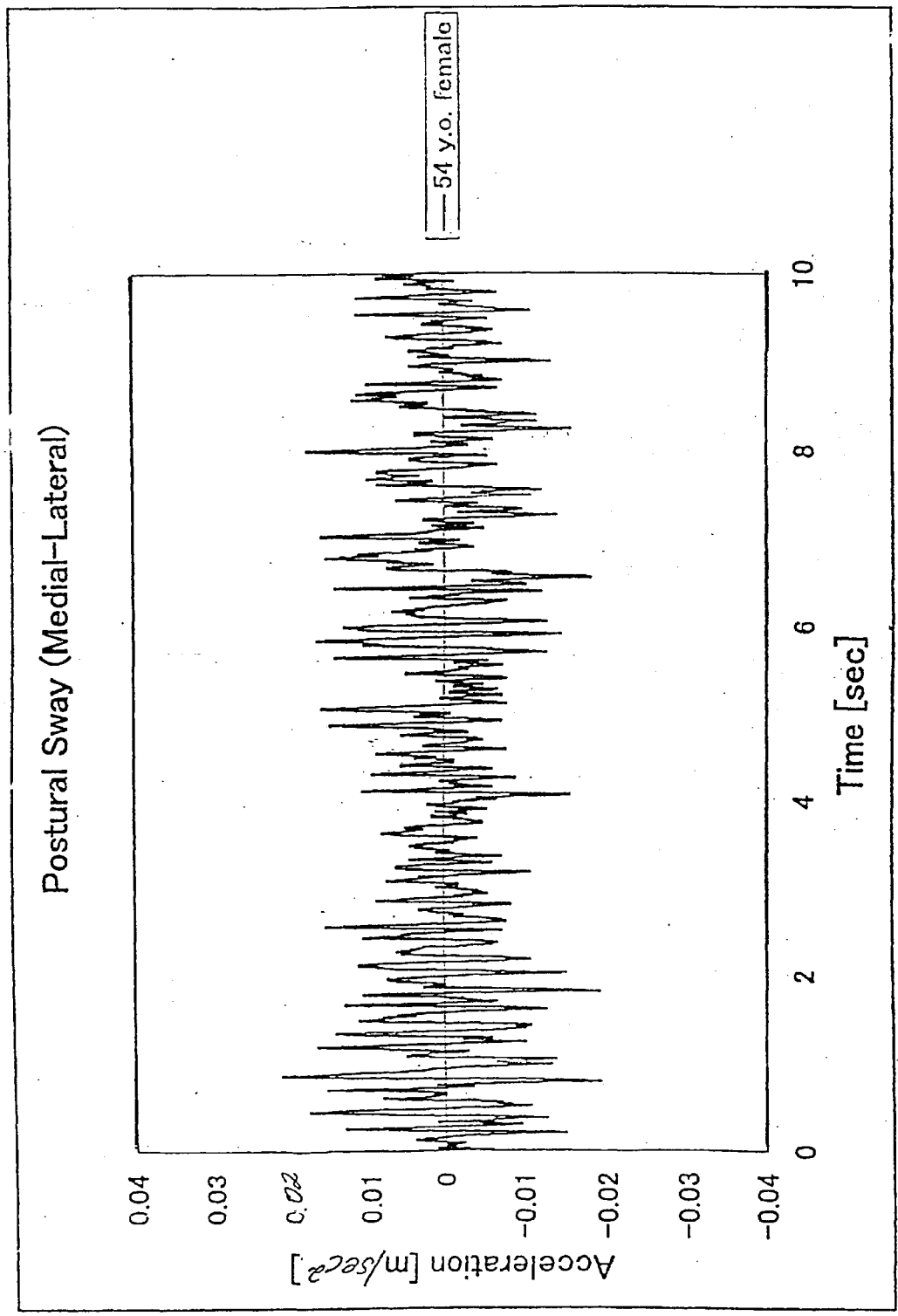

A typical sway pattern is seen in FIGS. 1 and 2, which compares the time dependent sway characteristics in a 23 year old woman to that in a 54 year old woman over a 10 second time course. It is clear that the older woman undergoes much greater swaying motion, though in general, the low frequency sway does not turn out to be a reliable indicator of postural stability.

Figure 3:
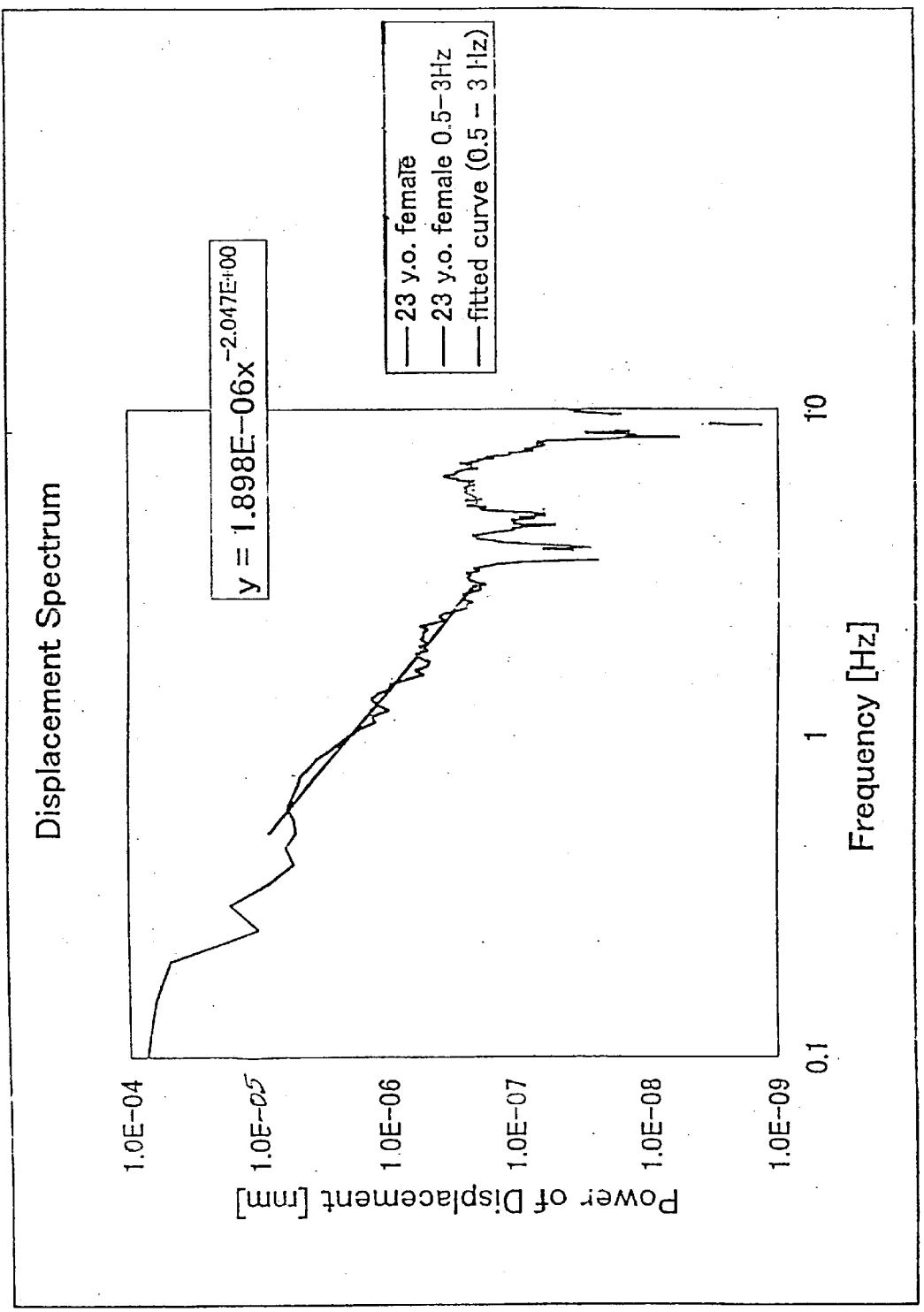
FIGS. 3 and 4 are charts illustrating spectral analysis of the sway data illustrated by FIGS. 1 and 2 in accordance with the method of the present disclosure.
Figure 4:
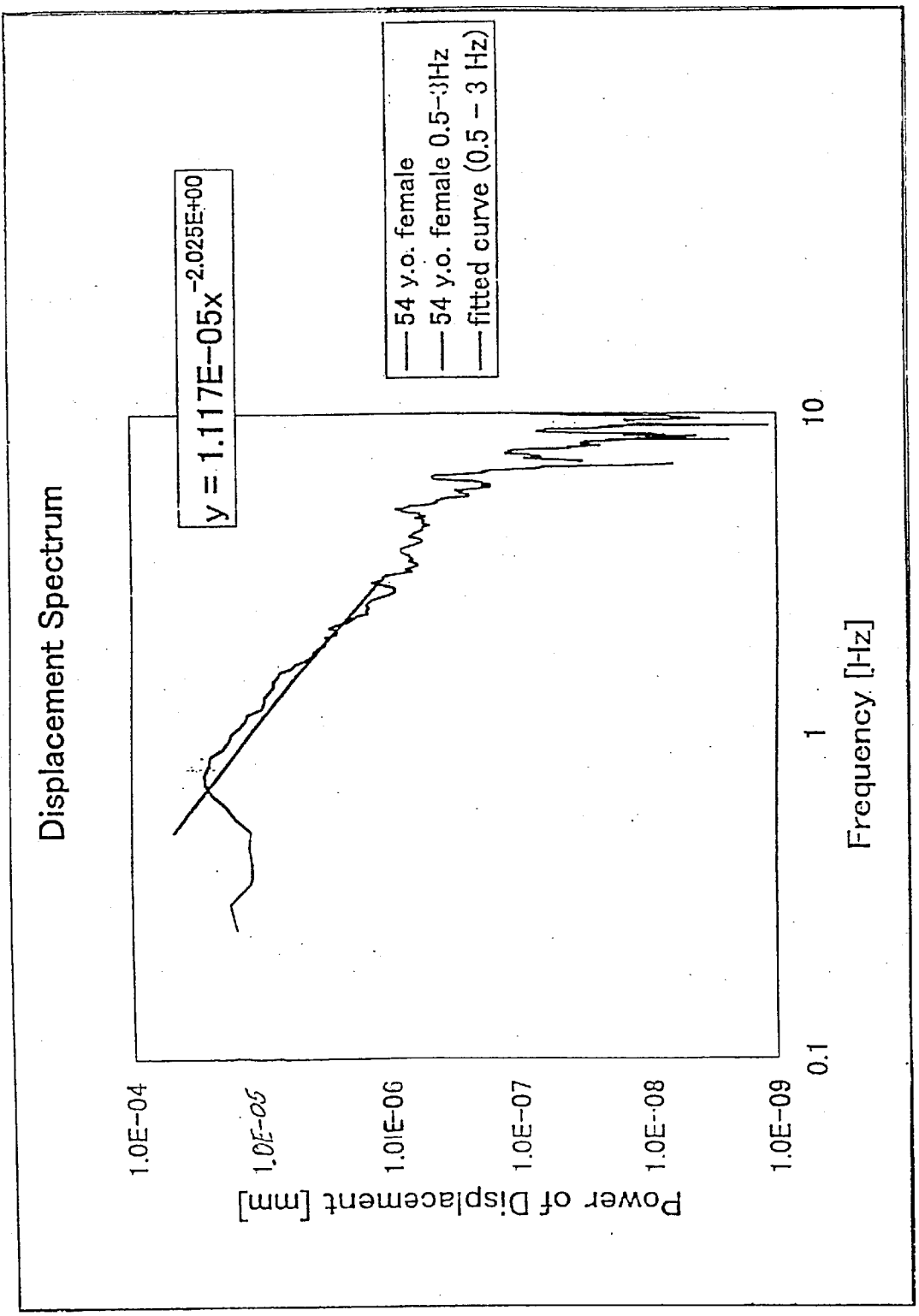

To quantify postural sway characteristics in accordance with the present disclosure, the time dependent sway pattern is filtered at 15 Hz, sampled at 51.2 Hz or higher, and then converted into the frequency domain following a third order correction to de-trend the data. Fourier analysis of the sway data demonstrates that sway is associated with a broad spectrum of frequency components. When the spectral analysis of the sway data are presented in a log—log format, the sway data frequency range is seen to extend from approximately 0.01 Hz to approximately 10 Hz (see FIGS. 3 and 4). Moreover, the pattern of sway magnitude versus frequency is distinctive, with sway magnitude decreasing monotonically, essentially in a linear manner, over these three decades of frequency, although depending on the spring constants of the springs supporting the platform, a system resonance may be evident in the spectral data.

Accordingly, the characteristics of an individual's sway can be reproducibly quantified in a relatively straightforward manner by determining the intercept of a regression line plotted through the sway spectral data (see FIGS. 3 and 4), presented on a log—log scale, with a predetermined (though relatively high) frequency. Preferably, a 3 to 10 Hz intercept is used.

The value of the regression line at the 3 Hz intercept provides a reproducible (coefficient of variation less than 20%) measure of postural sway which can clearly identify both the age related changes in postural sway, as well as being capable of identifying individuals with musculoskeletal pathologies.

The premise for the analysis is that decreased stability manifests itself in one of two ways, either through a general increase in sway at all frequencies, or through the individual adopting a stiff posture, which precludes large low frequency movements, but results in a jerky posture which contributes to the high frequency sway component. So, in all cases, decreased postural stability results in an increased high frequency sway content.

Figure 5:
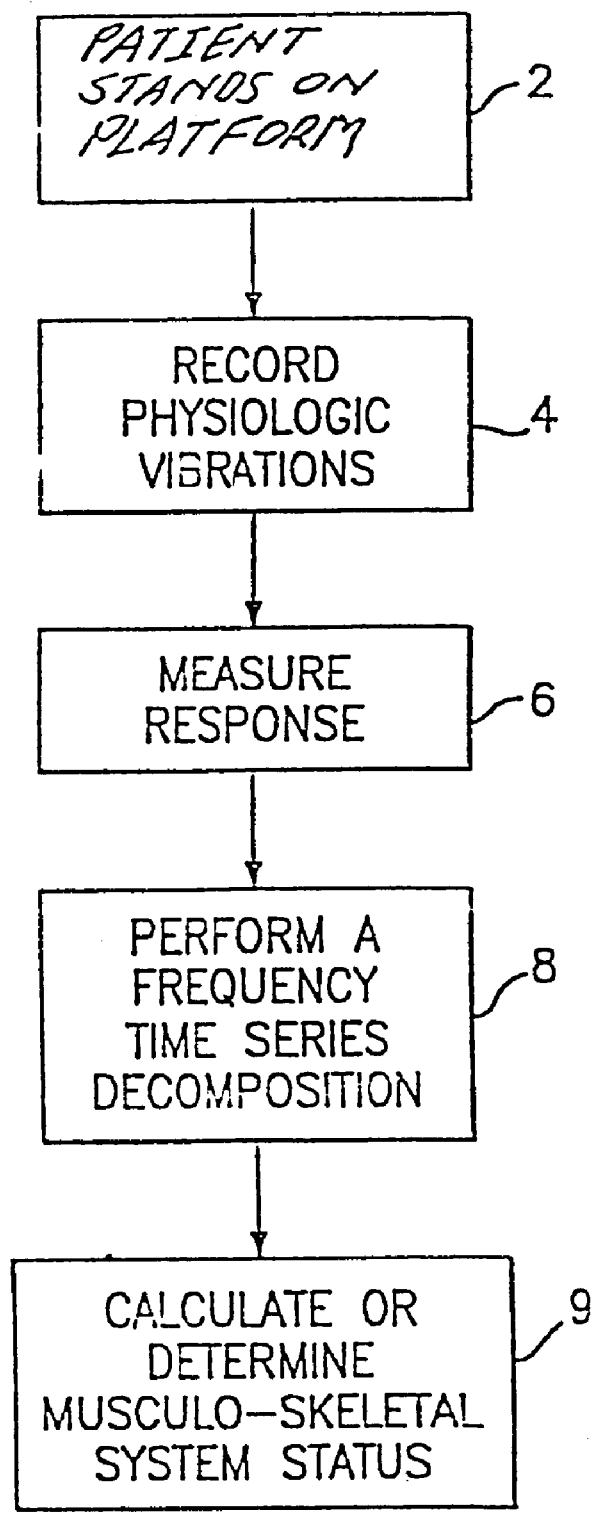
FIG. 5 is a flow diagram showing the steps for quantification of physiologic vibration in accordance with the method of the present disclosure.

Referring now in specific detail to the drawings in which like reference numerals identify similar or identical elements throughout the several views, and initially to FIG. 5, a flow diagram of the vibrational quantification method of the present disclosure is shown. In step 2, the patient stands on the standing platform having the at least one accelerometer mounted to the outboard side thereof. In step 4, activity is generated within at least one of the patient's muscle to create a measurable response from the musculoskeletal system. External vibrations and/or perturbation may be employed to create a measurable musculoskeletal response. This is particularly true for voluntary muscles which may have to be flexed to stimulate them. Involuntary muscles, such as postural muscles, typically do not require external stimulation and measurable signals can be produced without external vibration or perturbation. Step 6 represents measuring/recording the muscle response by, for example, recording musculoskeletal vibrations as indicated by the accelerometer. The measuring/recording is performed for a predetermined amount of time, e.g., between approximately 0.1 minute to 5 minutes.

In step 8, a frequency decomposition or other time series analysis/comparison is made to determine musculoskeletal status. Also, response data is compared to previously collected spectral response data. Previously collected spectral data includes data obtained for individuals with similar characteristics to the patient, for example age, sex, body measurements, etc. Further, postural sway or other neuromuscular characteristic may be quantified and compared. Step 9 determines a patient's postural stability based on the analysis of step 8.

Figure 6:
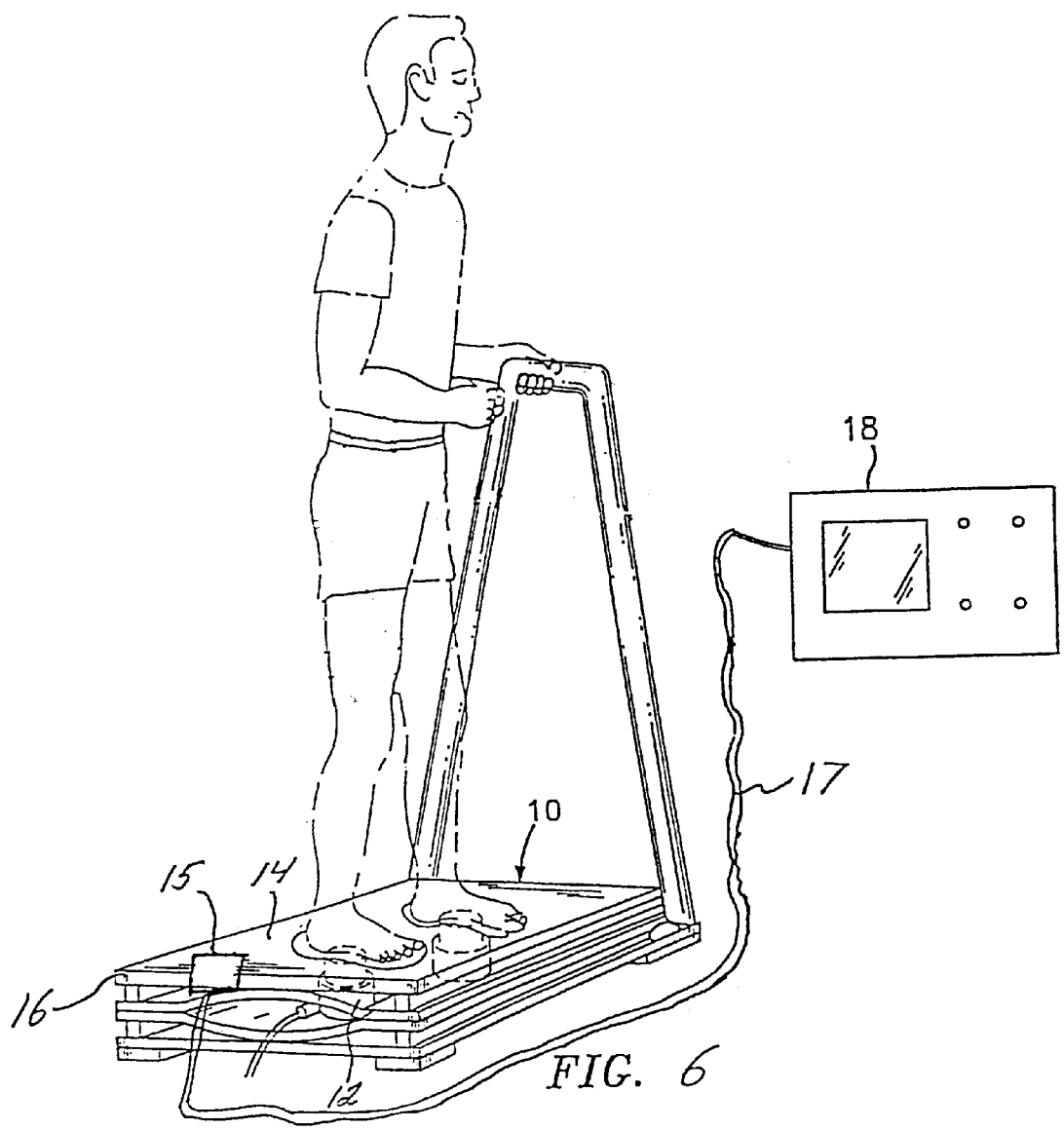
FIG. 6 is an isometric view showing a vibration table with a patient undergoing vibrational quantification in accordance with the system of the present disclosure.

FIG. 6 shows a vibration quantification apparatus system according to the present disclosure. A patient stands on a vibration table 10. Vibrations, generated by table 10 for a predetermined duration, for example, 0.5 to 5 minutes, are transmitted through the patient's body. The vibrations are generated by motorized spring mechanisms 12 located underneath a standing platform 14 of the vibration table 10 and attached thereto. It is contemplated that the vibrations may be generated by a plurality of non-motorized springs or coils attached underneath the standing platform 14, upon which the standing platform 14 rests.

The frequencies imparted by vibration table 10 are in the range between 0 and 100 Hz with a peak amplitude between 0.04 and 0.4 g's. The vibration waves are preferably sinusoidal, however other waveforms are contemplated. At least one accelerometer 15 is mounted to vibration table 10 on an outboard side 16 of the standing platform 14. Accelerometer 15 is used to measure the vibrational response of the patient's musculoskeletal system. During the vibration generation of vibration table 10, the response of accelerometer 15 can be amplified by a preamplifier (not shown) as known in the art.

Thereafter, the vibrational response is measured and recorded by spectrum analyzer/computer 18 which is electrically connected to accelerometer 15 by a cable 17. The accelerometer response data is analyzed to extract information on postural sway or other neuro-muscular characteristic. Accordingly, a determination is made regarding the postural stability of the patient.

Advantages provided by the method and system of the present disclosure is that little or no training/learning is required of the patients; pathologies in the ankles, knees, hips, sensory systems, spine, etc. can be identified; age-related changes in postural stability can be characterized; changes in postural stability following surgery can be characterized; improvements associated with rehabilitation therapy can be identified; postural capability can be characterized in individuals suspected of malingering; stability of an individual in the seated position can be characterized; the method and system of the present disclosure lend themselves to the patient being in a position other than the Romberg position; and the method and system of the present disclosure can be incorporated into therapeutic or exercise type devices to provide real-time feedback on improvements in postural stability while the patient is exercising or performing a task.

Having described preferred embodiments of a novel method and system for quantifying postural sway to determine postural instability or imbalance (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A non-invasive method for evaluating a musculoskeletal system of a patient comprising the steps of:

providing a vibration measurement device directly on a non-rigidly supported platform;

measuring a vibrational response of a patient's musculoskeletal system using the vibration measurement device after the patient rests on the non-rigidly supported platform;

performing a frequency decomposition of the vibrational response to quantify the vibrational response into specific vibrational spectra; and analyzing the vibrational spectra to evaluate at least postural stability.

2. The method as recited in claim 1, further comprising the step of determining postural stability by evaluating the vibrational response in a frequency range of below 5 Hz.

3. The method as recited in claim 1, wherein the vibration measurement device includes an accelerometer.

4. The method as recited in claim 1, wherein the step of analyzing the vibrational spectra includes the step of comparing the vibrational spectra to vibrational spectra of a same category.

5. The method as recited in claim 4, wherein the category includes at least one of age, sex and body measurement.

6. The method as recited in claim 1, wherein the step of measuring includes measuring the vibrational response of the neuro-muscular system for a predetermined amount of time.

7. The method as recited in claim 6, wherein the predetermined amount of time is between 0.1 minute to 5 minutes.

8. A non-invasive physiological vibration quantification system for evaluating a musculoskeletal system of a patient, the system comprising;

a non-rigidly supported vibration table;

vibration means for transferring vibrations to the musculoskeletal system and including an accelerometer for measuring a response by the musculoskeletal system in accordance with the vibrations transferred by the vibration means and for forming signals representative of the musculoskeletal system response, the accelerometer being mounted directly on the non-rigidly supported vibration table; and an analyzer coupled to the vibration measurement device for receiving the signals from the vibration measurement device and developing a frequency spectrum associated with the signals, the frequency spectrum providing vibrational quantification of the musculoskeletal system for evaluating at least postural stability.

9. The system as recited ion claim 8, wherein the vibration table generates frequencies amplitudes between 0 Hz to 100 Hz.

10. The system as recited ion claim 8, wherein the vibration table generates peak amplitudes between 0.04 g's tp 0.4 gs.

11. The system as recited in claim 8, wherein the vibration measurement device includes a solid state accelerometer.

12. The system as recited in claim 8, further comprising a recording means for recording vibrational responses of the patient's musculoskeletal system.

13. The system as recited in claim 8, wherein the frequency spectrum includes a response in a frequency range of below 10 Hz for determining postural stability.

14. A non-invasive method for evaluating a musculoskeletal system of a patient supported on a vibration table comprising the steps of:

transferring vibrations to the musculoskeletal system;

providing a vibration measurement device including an accelerometer directly on the vibration table for measuring a response by the musculoskeletal system in accordance with the vibrations transferred and for forming signals representative of the musculoskeletal system response; and developing a frequency spectrum associated with the signals, the frequency spectrum providing vibrational quantification of the musculoskeletal system for evaluating at least postural stability.

15. The method as recited in claim 14, wherein the step of transferring vibrations is performed while the patient is exercising.

16. The method as recited in claim 14, wherein the step of transferring vibrations is performed while the patient is either at rest or performing a task.

* * * * *